United States Patent [19]
Bona et al.

[11] Patent Number: 5,078,737
[45] Date of Patent: Jan. 7, 1992

[54] OBTURATOR FOR HEART VALVE PROSTHESES, A HEART VALVE PROSTHESIS PROVIDED WITH SUCH AN OBTURATOR, AND A METHOD FOR THE MANUFACTURE THEREOF

[75] Inventors: Gioachino Bona, Turin; Stefano Rinaldi, Parma; Franco Vallana, Turin, all of Italy

[73] Assignee: Sorin Biomedica S.p.A., Vercelli, Italy

[21] Appl. No.: 419,071

[22] Filed: Oct. 10, 1989

[30] Foreign Application Priority Data

Oct. 11, 1988 [IT] Italy .............................. 67909 A/88

[51] Int. Cl.⁵ ............................................. A61F 2/24
[52] U.S. Cl. ..................... 623/2; 137/512.1
[58] Field of Search .................... 623/2; 137/512.1

[56] References Cited

U.S. PATENT DOCUMENTS

| | | | |
|---|---|---|---|
| 3,926,215 | 12/1975 | Macleod | 623/2 |
| 4,254,508 | 3/1981 | Bokros . | |
| 4,308,624 | 1/1982 | Klawitter | 623/2 |
| 4,451,937 | 6/1984 | Klawitter . | |
| 4,888,010 | 12/1989 | Bokros | 623/2 |

FOREIGN PATENT DOCUMENTS

| | | | |
|---|---|---|---|
| 0176337 | 4/1986 | European Pat. Off. . | |
| 0211576 | 2/1987 | European Pat. Off. . | |
| 3028981 | 7/1980 | Fed. Rep. of Germany . | |
| 8900033 | 1/1989 | PCT Int'l Appl. | 623/2 |

*Primary Examiner*—Randy C. Shay
*Attorney, Agent, or Firm*—George P. Hoare, Jr.

[57] ABSTRACT

The thickness of the obturator (3) increases gradually from the central region ($C_9$, $C_{10}$) towards the ends ($P_9$, $P_{10}$) of the edge (6) nearest to the axis of articulation (5) to the prosthesis, and decreases gradually or is constant from that edge to the other end edge (7) which forms the outer edge of the obturator.

6 Claims, 3 Drawing Sheets

OBTURATOR FOR HEART VALVE PROSTHESES, A HEART VALVE PROSTHESIS PROVIDED WITH SUCH AN OBTURATOR, AND A METHOD FOR THE MANUFACTURE THEREOF

FIELD OF THE INVENTION

The present invention relates in general to heart valve prostheses (heart valves for short) including at least one obturator which is mounted in the stent of the prosthesis so that it can pivot between a closed position in which the obturator obstructs the flow of blood through the prosthesis in one direction, and an open position in which the obturator allows the blood to flow freely in the opposite direction.

The invention has been developed with particular attention to its possible use in the field of heart valve prostheses including a generally-annular stent within which two generally fingernail- or eyelid-shaped obturators (leaflets) are mounted so as to be pivotable under the effect of the blood flow.

Heart valve prostheses of this type (usually defined as bi-leaflet valves) are described, for example, in European patent Nos. 0023797 and 0113681, as well as in European Patent Application Nos. 0327790 and 0338179, the latter two being in the name of the same Applicant.

The production of obturators for such valve prostheses must take account of many concomitant and frequently conflicting factors, such as:

the need to ensure that the obturators, which in some cases are snap-mounted in their positions of articulation in the stent, have good structural strength (particularly bending strength), the need to minimise the moment of rotational (pivoting) inertia of the obturators in order to keep the opening and closing times as short as possible, and thus minimise pressure loss and reflux so that the operating characteristics resemble those of natural heart valves as closely as possible, the imperative need to ensure that the regions where the obturator is connected (articulated) to the stent can withstand the stresses of operation throughout the useful life envisaged for the prosthesis without wearing out: any failure of the obturator, or even simply jamming of its pivoting movement, would in fact be fatal for the patient in whom the prosthesis is fitted, the need to give the obturator a good dynamic profile with the primary object of making the angle of opening of the obturator as wide as possible, so that it also offers minimum resistance to the flow of blood through the prosthesis and at the same time limits the time taken for the obturators to return to the closed position.

SUMMARY OF THE INVENTION

The present invention aims to provide a heart valve prosthesis (particularly, but not exclusively, a bi-leaflet prosthesis) which meets all the requirements set out above in the best possible manner.

According to the present invention, this object is achieved by virtue of an obturator for heart valve prostheses which has the characteristics recited in the claims that follow.

The invention also relates to a heart valve prosthesis provided with one or more obturators having the aforesaid characteristics, as well as to a method for the manufacture of such obturators.

In general terms, in the preferred embodiment of the invention, the thickness of the obturator increases gradually from the central region of the edge near the axis about which the obturator pivots between the open and closed positions towards the vertices of this edge, in correspondence with which the obturator is articulated to the stent of the prosthesis, and decreases or is constant from that edge to the opposite edge which forms the outer edge of the obturator.

This solution has turned out to be the best as far as the possibility of simultaneously fulfilling all the requirements set out above is concerned, providing an obturator which, whilst having a minimal moment of inertia about its pivot axis and achieving very wide opening angles with minimal flow resistance when opening, at the same time provides intrinsic structural strength both as regards bending and as regards resistance to stresses and wear in the regions of its articulation to the stent of the prosthesis.

BACKGROUND OF THE INVENTION

As regards the thickening of the edge near the articulation axis towards the two articulation vertices, it may be noted that European patent Nos. 0023797 and 0113681 (see, in particular, FIG. 8 of both the patents in question) show bi-leaflet valve obturators of constant thickness, the end articulation regions of which are slightly thicker than the obturator which is nevertheless of strictly constant thickness. The obturators described in the prior documents thus lack the progressive increase in thickness from the centre towards the vertices which, in the obturator according to the invention, is present in addition to or instead of the progressive reduction in the thickness of the obturator between its two opposite edges.

The invention will now be described, purely by way of non-limiting example, with reference to the appended drawings, in which:

Figure 1:
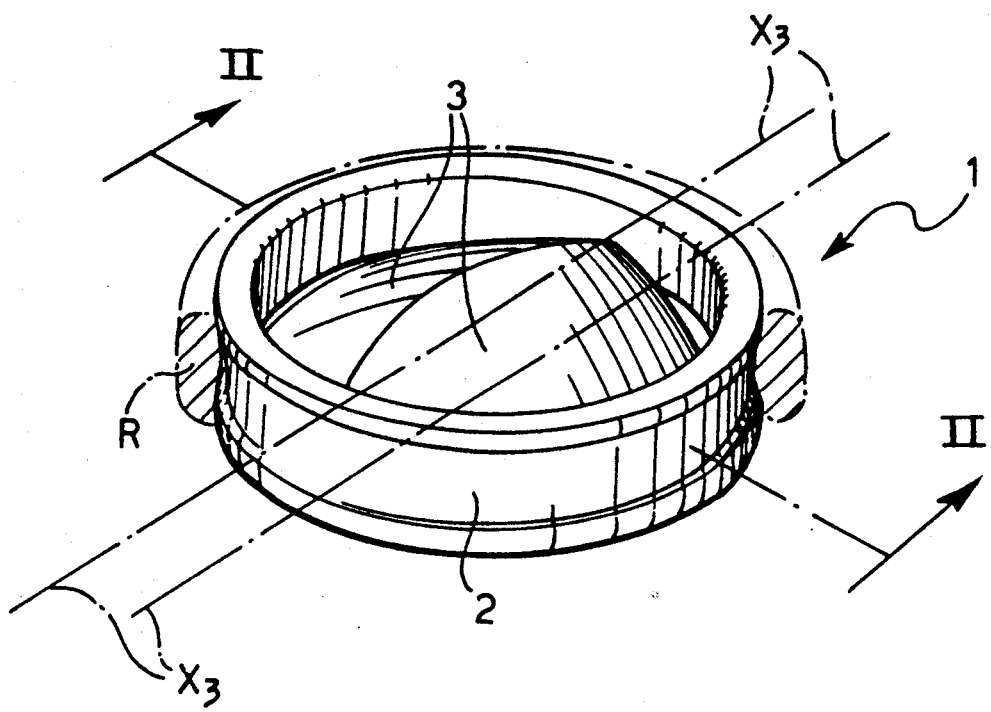
FIG. 1 is a perspective view of a heart valve prosthesis produced according to the invention.

In the drawings, a heart valve prosthesis, generally indicated 1, is intended to be used to replace a natural heart valve (for example, the aortic valve or the mitral valve) which is suffering from damage or heart disease.

DETAILED DESCRIPTION OF THE INVENTION

According to a know solution prosthesis 1 comprises:
a generally-annular stent 2 defining a passage for the blood, and
a plurality of obturators (usually two), indicated 3, having a general eyelid or fingernail shape.

Figure 2:
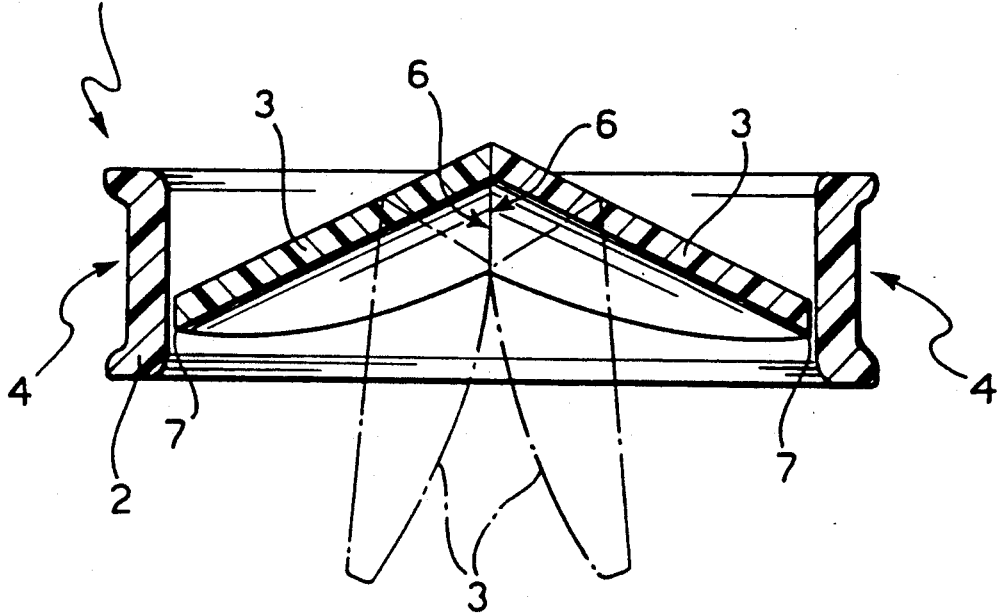
FIG. 2 is a section taken on the line II—II of FIG. 1, on an enlarged scale.

The obturators (leaflets) 3 are mounted in the stent so that they can pivot between a closed position (shown in continuous outline in FIG. 2) and an open position (shown in broken outline, also in FIG. 2). For the purposes of the present description and the claims which follow, it is assumed that this pivoting movement can be defined as a movement which takes place about respective diametral lines (more precisely, subdiametral lines) which can be identified—at least approximately—by axes $X_3$ (see FIG. 1).

These axes may be fixed relative to the stent of the prosthesis 2 or, according to solutions already proposed and tested in the past:

may be able to effect a general rotational movement around the circumference of the stent 2;

may be able to move gradually during the pivoting of the obturators 3, which thus takes place about an axis that moves continuously along a straight, arcuate or falcate path as the obturator pivots.

In any case, the criteria used for the connection (articulation) of the obturators 3 to the stent 2 are not specifically relevant to the understanding of the present invention and will not therefore be described in detail below.

In the open position, the obturators 3 extend in positions almost perpendicular to the general plane of the stent 2 and thus enable the blood to flow freely through the prosthesis in a first direction (downwards with reference to the orientation of FIG. 2).

When the direction of the blood flow is reversed by the action of the heart muscle, the blood pressure automatically brings the obturators 3 into the closed position in which the obturators 3 together occlude the orifice of the prosthesis, preventing the blood from flowing in the opposite direction (upwards with reference to the orientation of FIG. 2).

The stent 2 is made from a rigid biocompatible material, for example, metal or a carbonaceous material, or even a combination of the two (a metal core covered by carbonaceous material, or carbonaceous material with a metal reinforcing structure). The stent 2 usually has a groove 4 in its outer surface for facilitating the mounting of a suture ring around the stent 2. This enables the prosthesis to be fixed to the annulus of the natural valve after the removal of its valve flaps. The profile of the suture ring R, which is made from a textile of biocompatible yarn (for example, yarn made from the materials known under the trade names of Dacron or Teflon), is shown schematically in broken outline in FIG. 1 only.

The obturators 3 may be constituted by a core (for example, of graphite) covered with a layer of biocompatible carbonaceous material deposited by high-temperature pyrolysis (pyrocarbon) or by means of a vapour-phase deposition method. Alternatively, the obturators 3 may be made entirely of carbonaceous material and other biocompatible materials. Similar layers of biocompatible carbonaceous material may also be applied to the stent 2 and to the suture ring R, at least on the parts intended to be exposed to the blood flow.

Figure 3:
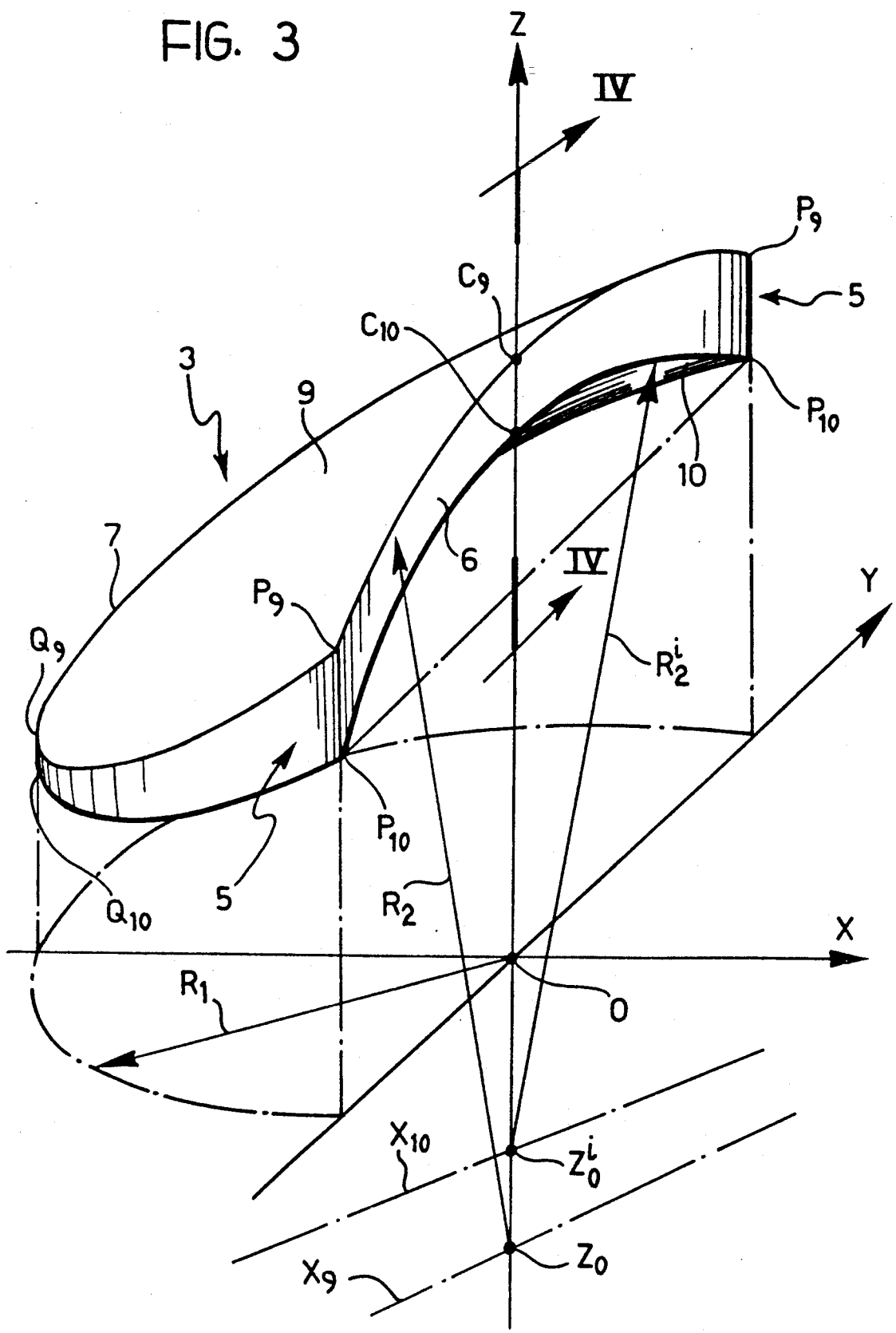
FIG. 3 is a perspective view of one of the parts shown in FIGS. 1 and 2 on an even larger scale, showing specifically the geometric parameters of the part in question.

As can better be seen in the perspective view of FIG. 3, the obturators 3 are generally eyelid- or fingernail-shaped and each can be seen to have:

two opposing vertices 5 which define the regions in correspondence with which the obturators 3 pivot about the respective axes $X_3$ once they are mounted in the stent 2 (as far as the specific criteria used for the articulation of the obturators 3 to the stent and the possibility of any movement of the axes $X_3$ are concerned, reference may be made to any prior-art solution, as already mentioned by way of a preamble in the introduction to the present description), a first end edge 6 of the prosthesis, which is generally flat (but may be rounded at its lower corner) and extends between the vertices 5 in an arcuate arrangement, thus constituting the "inner" edge of the obturator 3, that is, the edge near the pivot axis $X_3$, a second end edge which extends between the vertices 5 along a generally arcuate path so as to define the outer edge of the obturator 3 (that is, the edge remote from the pivot axis $X_3$) and is intended to cooperate with the profile of the stent 2 in the closed position, as shown in FIG. 2, and two major surfaces, a convex upper surface 9 and a concave lower surface 10 respectively, which define the two opposing surfaces of the obturator over which the blood is intended to flow.

More precisely, the blood is intended to flow over the upper surface 9 during the opening movement, whilst the lower surface 10 is that against which the blood pressure acts during the closure of the valve.

In the obturator according to the invention, both the surfaces 9 and 10 are constituted by substantially cylindrical surfaces each having a respective radius of curvature and a respective principal axis.

Figure 4:
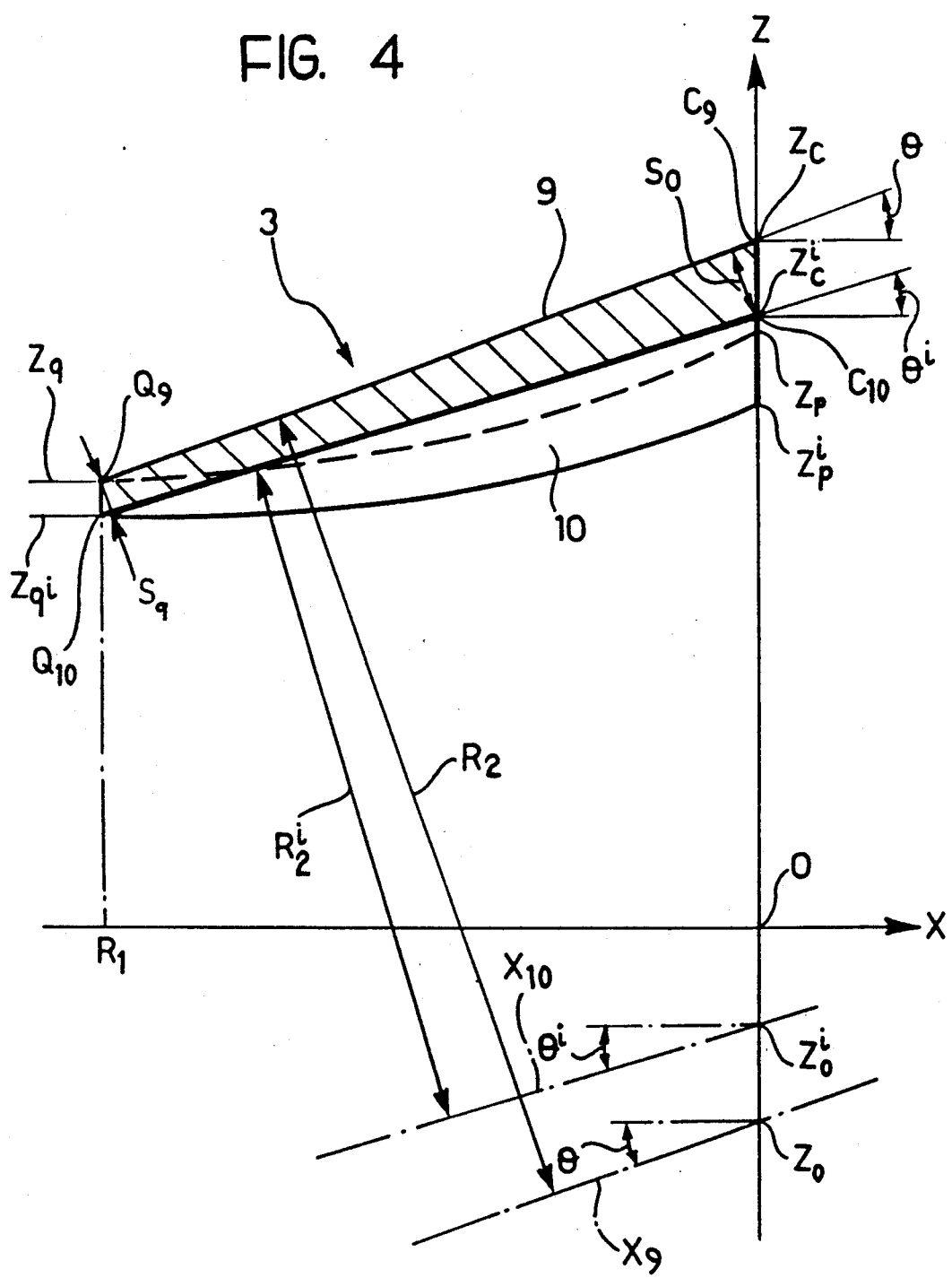
FIG. 4 is a section taken in the plane indicated by the arrows IV—IV of FIG. 3.

In FIGS. 3 and 4, the two radii of curvature in question are indicated $R_2$ for the upper surface 9 and $R_2^i$ for the lower surface 10.

Similarly, the two principal axes are indicated $X_9$ and $X_{10}$ respectively.

The term "substantially cylindrical" applied to the surfaces 9 and 10 in the present description and in the claims which follow is intended to apply not only to strictly cylindrical surfaces, but also generally to surfaces which, although not being exactly cylindrical overall, have an arcuate shape (for example, an elliptical profile) which is sufficiently regular to enable the definition of an average radius of curvature and of a locus of the centres of curvature gathered around an axis.

The analytical criteria for defining the geometrical characteristics of the obturators 3 will now be described more specifically with reference to FIGS. 3 and 4, in which an obturator 3 according to the invention is shown in a system of cartesian coordinates (O, x, y, z) with the inner or front edge 6 of the obturator 3 arranged in the plane $x=0$. The obturator 3 is also located such that its outer or rear edge 7 defines a circular projection with a radius $R_1$ in the plane $z=0$ (which is generally considered to identify a plane parallel to that containing the stent 2 of the prosthesis against which the obturator 3 is intended substantially to form a seal in the closed position).

It is also assumed that the two principal axes $X_9$ and $X_{10}$ extend in the plane $y=0$ at respective angles $\theta$ and $\theta^i$ to the x axis.

The geometry of the upper surface 9 of the obturator 3 is determined on the basis of the flow conditions and conditions of a functional character, such as: the desired angle of pivoting between the open and closed positions of the obturator, the maximum depth of the cross-section of the valve, the conditions of the blood flow through the valve orifice (its centrality and distribution in the aperture), etc.

This leads to the determination of the radius $R_2$ of the cylinder which generates this surface, its inclination ($\theta$) to the plane of the valve (that is, to the x axis) and the point $Z_0$ where this axis intersects the central axis of the valve stent which is perpendicular to the plane of the valve, that is, the Z axis shown in FIGS. 3 and 4.

The obturator 3 is delimited in the plane yz by the surface of its front or inner edge 6 having the equation:

$$x=0 \tag{1}$$

whilst it is defined at its rear or outer edge 7 by the cylinder defined by the equation $$x^2 + y^2 = R_1^2 \quad (2)$$

that is, by a cylinder of radius $R_1$ whose principal axis coincides with the z axis. Naturally, it will generally be true that $R_1 < R_2$.

The equation of the axis $X_9$ which defines the upper surface 9 of the obturator 3 can be expressed in the form:

$$\begin{cases} y = 0 \\ z = z_o + x \tan \theta \end{cases} \quad (3)$$

so that the aforesaid cylinder defining the upper surface can be described in parametric form as $$\begin{cases} y = a \\ z = z_o + x \cdot \tan \theta \pm \dfrac{\sqrt{(R_2)^2 - (a)^2}}{\cos \theta} \end{cases} \quad (4)$$

where a is an arbitrary parameter.

The central point $C_9$ and the ends $P_9$ of the upper surface 9 which are situated in correspondence with the inner or front edge 6, as well as the central point $Q_9$ of the same surface situated in correspondence with its rear edge 7, are defined by the coordinates:

$$C_9 \rightarrow x=0;\ y=0;\ Z=Z_c \quad (5)$$

$$P_9 \rightarrow x=0;\ y=\pm R_1;\ Z=Z_p \quad (6)$$

$$Q_9 \rightarrow x=-R_1;\ y=0;\ Z=Z_q \quad (7)$$

from which, on the basis of the above equations, the following expressions can be derived for the respective Z coordinates $$C_9 \rightarrow Z_c = Z_o + \dfrac{R_2}{\cos \theta} \quad (8)$$

$$P_9 \rightarrow Z_p = Z_o + \dfrac{\sqrt{(R_2)^2 - (R_1)^2}}{\cos \theta} \quad (9)$$

$$Q_9 \rightarrow Z_q = Z_o + \dfrac{R_2}{\cos \theta} - R_1 \cdot \tan\theta \quad (10)$$

Wholly analogous equations are true for the cylindrical surface defining the lower surface 10 of the obturator (of which the central points of the edges 6 and 7 are indicated $C_{10}$ and $Q_{10}$, respectively, and the ends are indicated $P_{10}$) and are obtained simply by the following substitutions:

$x = > x^i$
$y = > y^i$
$z = > z^i$
$R_2 = > R_2^i$
$\theta = \theta^1$ where, in general, $R_2 > R_2^i$; $\theta > \theta^i$ and $|Z_O| > |Z_O^i|$.

In other words, this means that:

the radius of curvature $R_2$ of the upper surface 9 is greater than the radius of curvature $R_2^i$ of the lower surface 10, the principal axes $X_9$ and $X_{10}$ generally converge from the outer or rear edge 7 towards the inner or front edge 6, or at most are parallel, and the principal axis $X_{10}$ of the cylindrical surface constituting the lower surface 10 is nearer the obturator 3 than the principal axis $X_9$ of the upper surface 9.

In practice, this means that the front or inner edge 6 is thinnest in correspondence with the central region of the obturator (the points $C_9$, $C_{10}$) and becomes regularly and progressively thicker towards the ends of the edge (the points $P_9$, $P_{10}$), whilst retaining the general symmetry of the obturator about the plane $y=0$, and the thickness of the obturator 3 decreases gradually or is constant from the front or inner edge 6 ($C_9$, $C_{10}$) to the rear or outer edge 7 ($Q_9$, $Q_{10}$).

In particular, with reference to the symbols used in FIG. 4, where:

($z_c - z_c^i$) represents the distance between the points $C_9$ and $C_{10}$ in correspondence with the centre of the inner or front edge 6, ($z_p - z_p^i$) represents the distance between the points $P_9$ and $P_{10}$ at the two vertices 5 and ($z_q - z_q^i$) represents the distance between the points $Q_9$ and $Q_{10}$ in correspondence with the centre of the outer rear edge 7, the following equations are obtained:

$$(z_c - z_c^i) = (z_o - z_o^i) + \dfrac{R_2}{\cos \theta} - \dfrac{R_2^i}{\cos \theta^i} \quad (12)$$

$$S_o = (z_o - z_o^i) \cdot \cos \theta - R_2 - R_2^i \cdot \dfrac{\cos \theta}{\cos \theta^i} \quad (13)$$

$$(z_p - z_p^i) = (z_o - z_o^i) + \dfrac{\sqrt{(R_2)^2 - (R_1)^2}}{\cos \theta} - \dfrac{\sqrt{(R_2)^i - (R_1)^2}}{\cos \theta^i} \quad (14)$$

$$(z_q - z_q^i) = (z_o - z_o^i) + \left( \dfrac{R_2}{\cos \theta} - \dfrac{R_2^i}{\cos \theta^i} \right) - R_1 (\tan \theta - \tan \theta^i) \quad (15)$$

$$S_q = (z_q - z_q^i) \cdot \cos \theta \quad (16)$$

where $S_o$ and $S_q$ represent the thickness of the obturator in correspondence with the central regions of the front or inner edge 6 and the rear and outer edge 7, measured in a direction generally perpendicular to the axis $X_9$ which generates the upper surface 9.

The quantities $S_o$ and $S_q$ constitute design parameters which are preferred to the distances ($z_c - z_c^i$) and ($z_q - z_q^i$) in the design definition of the characteristics of the valve, since they are more readily derived from thickness of the actuator in the general direction of its development.

In general, the aforesaid parameters are selected according to the following criteria:

the definition of the physical characteristics of the obturator 3 as regards its structural strength, with specific attention to bending strength, bearing in mind the general arcuate shape of the obturator 3, and the consequent definition of the "desired" values of $S_o$ and $S_q$, the minimisation of the moment of pivoting inertia of the obturator 3 about the axis (or the locus of the axes) $X_3$: this minimisation usually involves the selection of the smallest value of $S_q$ compatible with the structural requirements taken into consideration in the previous step, the analysis of the geometric and structural requirements dictated by the configuration of the articulation of the obturators 9 to the stent 2 and by the stresses resulting therefrom, with the consequent need to maximise the distance or thickness $(z_p - z_p^i)$ at the vertices 5 without an appreciable increase in the overall cross-section of the obturator 3 and its moment of pivoting inertia, and the definition of the best hydrodynamic profile of the obturator 3 in order to achieve the maximum opening angle (the least flow resistance when open) and restrict the closure time.

Values which have been found to be particularly advantageous for an obturator 3 constituted by a graphite core covered with a layer of biocompatible carbonaceous material are as follows:

$$S_o = 1.0 \text{ mm}, S_q = 1.2 \text{ mm}, (z_p - z_p^i) = 1.6 \text{ mm}.$$

The above dimensional values having been defined, the equations (12) to (17) can easily be inverted in order to determine the geometric parameters $R_2^i$, $z_o^i$ and $theta^i$ of the cylindrical (or substantially cylindrical) surface defining the lower surface 10 of the obturator which satisfies the conditions set.

By following the method described, it is possible to design an obturator 3 for heart valve prostheses which, as well as satisfying the various requirements referred to in the introduction to the present description extremely well, has the further advantage that it is delimited by well-defined, geometrically-simple surfaces, which makes its manufacture considerably easier.

We claim:

1. An obturator for heart valve prostheses, including a convex upper surface and a concave lower surface which are intended to be exposed to the blood flow, in use, in order to cause the obturator to orient between an open position and a closed position about an offset subdiametrical pivot axis, the obturator having a first near pivot axis end edge and a second remote pivot axis end edge which are near to and remote from the pivot axis respectivley, wherein said upper and lower surfaces are substantially cylindrical surfaces each having a respective radius of curvature ($R_2$; $R_2^i$) and a respective principal axis ($X_9$, $X_{10}$) each principal axis being perpendicular to the offset pivot axis and substantially cylindrical surfaces satisfy at least one of the following conditions:

the radius of curvature ($R_2$) of the upper surface is greater than the radius of curvature ($R_2^i$) of the lower surface so that the thickness of the first near pivot axis end edge increases generally from its central region towards its end regions, and the principal axes ($X_9$, $X_{10}$) converge generally from the second remote pivot axis end edge to the first near pivot axis end edge so that the thickness of the obturator decreases generally from the first near pivot axis end edge towards the second remote pivot axis end edge.

2. An obturator for heart valve prostheses according to claim 1, wherein the radius of curvature ($R_2$) of the upper surface is greater than the radius of curvature ($R_2^i$) of the lower surface, the principal axis ($X_{10}$) of the lower surface being nearer the obturator than the principal axis ($X_9$) of the upper surface.

3. A heart valve prosthesis including at least one obturator having a convex upper surface and a concave lower surface which are intended to be exposed to the blood flow, in use, in order to cause the obturator to orient between an open position and a closed position about an offset pivot axis, the obturator having a first near pivot axis end edge and second remote pivot axis end edge which are near to and remote from the pivot axis respectively, wherein said upper and lower surfaces are substantially cylindrical surfaces each having a respective radius of curvature ($R_2$; $R_2^i$) and a respective principal axis ($X_9$, $X_{10}$), each principal axis being perpendicular to the offset pivot axis said substantially cylindrical surfaces satisfy at least one of the following conditions:

the radius of curvature ($R_2$) of the upper surface is greater than the radius of curvature ($R_2^i$) of the lower surface so that the thickness of the first near pivot axis end edge increases generally from its central region towards its end regions, and the principal axes ($X_9$, $X_{10}$) converge generally from the second remote pivot axis end edge to the first near pivot axis end edge so that the thickness of the obturator decreases generally from the first near pivot axis end edge towards the second remote pivot axis end edge.

4. A prosthesis according to claim 3, including two of said obturators.

5. A method for manufacturing obturators for heart valve prostheses, including a convex upper surface and a concave lower surface which are intended to be exposed to the blood flow, in use, in order to cause the obturator to orient between an open position and a closed position about an offset subdiametrical pivot axis, the obturator having a first near pivot axis end edge and a second remote pivot axis end edge which are near to and remote from the pivot axis respectively, said method including the steps of:

forming the upper surface in the form of a substantially cylindrical surface with a respective radius of curvature ($R_2$) and a respective principal axis ($X_9$) which is perpendicular to the offset pivot axis, forming the lower surface in the form of a substantially cylindrical surface which also has a respective radius of curvature ($R_2^i$) and a respective principal axis ($X_{10}$) which is perpendicular to the offset pivot axis and satisfies at least one of the following conditions:

the radius of curvature ($R_2^i$) of the lower surface is less than the radius of curvature ($R_2$) of the upper surface, and the principal axis ($X_{10}$) of the lower surface converges generally toward the principal axis ($X_9$) of the upper surface from the second end edge towards the first edge.

6. A method according to claim 5, wherein the lower surface is formed so as to satisfy the following conditions in combination:

the radius of curvature ($R_2^i$) of the lower surface is less than the radius of curvature ($R_2$) of the upper surface, and the principal axis ($X_{10}$) of the lower surface is nearer to the actuator than the principal axis ($X_9$) of the upper surface.

* * * * *